(12) United States Patent
Habrich et al.

(10) Patent No.: US 10,335,794 B2
(45) Date of Patent: Jul. 2, 2019

(54) DEVICE, SYSTEM AND METHOD FOR COOLING A REAGENT COMPARTMENT

(71) Applicant: STRATEC Biomedical AG, Birkenfeld (DE)

(72) Inventors: Stephan Habrich, Bad Wildbad (DE); Martin Trump, Pforzheim (DE)

(73) Assignee: STRATEC SE, Birkenfeld (DE)

( * ) Notice: Subject to any disclaimer, the term of this patent is extended or adjusted under 35 U.S.C. 154(b) by 0 days.

(21) Appl. No.: 15/173,990

(22) Filed: Jun. 6, 2016

(65) Prior Publication Data

US 2016/0354784 A1 Dec. 8, 2016

(30) Foreign Application Priority Data

Jun. 5, 2015 (GB) .................................. 1509789.2

(51) Int. Cl.
| | |
|---|---|
| *B01L 7/00* | (2006.01) |
| *F25D 21/14* | (2006.01) |
| *F25D 17/06* | (2006.01) |
| *G01N 35/00* | (2006.01) |
| *F25B 21/02* | (2006.01) |

(52) U.S. Cl.
CPC ................ *B01L 7/00* (2013.01); *F25B 21/02* (2013.01); *F25D 17/06* (2013.01); *F25D 21/14* (2013.01); *G01N 35/00* (2013.01); *B01L 2200/16* (2013.01); *B01L 2300/1822* (2013.01); *B01L 2300/1844* (2013.01); *B01L 2300/1894* (2013.01); *F25B 2321/023* (2013.01); *F25B 2321/0251* (2013.01); *G01N 2035/00445* (2013.01)

(58) Field of Classification Search
CPC .................. B01L 7/00; B01L 2200/16; B01L 2300/1894; B01L 2300/1844; G01N 35/00; G01N 2035/00445; F25B 21/02; F25B 2321/023; F25B 2321/0251; F25D 17/06; F25D 21/14
USPC ........................................................... 62/3.2
See application file for complete search history.

(56) References Cited

U.S. PATENT DOCUMENTS

| | | | | |
|---|---|---|---|---|
| 4,364,234 | A | | 12/1982 | Reed |
| 4,456,581 | A | * | 6/1984 | Edelmann ............. B01F 5/0641 356/246 |
| 4,954,237 | A | * | 9/1990 | Sarrine ............ G01N 27/44708 204/608 |

(Continued)

FOREIGN PATENT DOCUMENTS

| | | |
|---|---|---|
| DE | 20 2014 104 040 U1 | 9/2014 |
| EP | 2500732 A2 | 9/2012 |
| JP | 2004 205052 A | 7/2004 |

*Primary Examiner* — Kun Kai Ma
(74) *Attorney, Agent, or Firm* — 24IP Law Group USA, PLLC; Timothy R DeWitt

(57) ABSTRACT

The present invention is directed to a device, system and method for cooling a reagent compartment. The invention also relates to a use of the device. The device comprises a housing with a first side for attachment to the reagent compartment, a cooling unit with at least one cooling element with a warm upper side and a cold lower side, that is equipped with a cold side heat exchanger comprising at least one first fan, a at least one cold air channel and at least one cold air opening at the first side of the housing for circulating cold air between the at least one cooling element and the reagent compartment in a closed system.

12 Claims, 23 Drawing Sheets

(56) References Cited

U.S. PATENT DOCUMENTS

| | | | | |
|---|---|---|---|---|
| 5,460,709 | A * | 10/1995 | Sarrine | G01N 27/44782 |
| | | | | 204/607 |
| 6,019,098 | A * | 2/2000 | Bass | F24H 1/00 |
| | | | | 126/344 |
| 6,370,882 | B1 | 4/2002 | Adamski et al. | |
| 2006/0204950 | A1 * | 9/2006 | Ilercil | A01N 1/02 |
| | | | | 435/1.1 |
| 2008/0063573 | A1 * | 3/2008 | Ammann | B01L 7/52 |
| | | | | 422/105 |
| 2010/0248346 | A1 * | 9/2010 | Kaneko | G01N 35/1002 |
| | | | | 435/287.1 |
| 2011/0025211 | A1 * | 2/2011 | Bae | F21V 29/004 |
| | | | | 315/113 |
| 2011/0197598 | A1 * | 8/2011 | Cheng | H01L 23/3675 |
| | | | | 62/3.6 |
| 2011/0236259 | A1 * | 9/2011 | Mototsu | B01L 3/52 |
| | | | | 422/63 |
| 2011/0253224 | A1 * | 10/2011 | Linder | B01L 3/5027 |
| | | | | 137/2 |
| 2013/0160533 | A1 * | 6/2013 | Fukuma | G01N 35/00 |
| | | | | 73/64.56 |

* cited by examiner

DEVICE, SYSTEM AND METHOD FOR COOLING A REAGENT COMPARTMENT

CROSS-REFERENCE TO RELATED APPLICATIONS

The present application claims priority of British Patent Application No. GB 1509789.2 filed on Jun. 5, 2015. The aforementioned application is hereby incorporated by reference in its entirety.

BACKGROUND OF THE INVENTION

Field of the Invention

The present invention is directed to a device, system and method for cooling a reagent compartment. The invention also relates to a use of the device.

Brief Description of the Related Art

Automated analyzer systems typically incorporate modules for loading, storage, and unloading of reagent fluids. The reagent fluids are usually comprised in a reagent compartment, and the temperature of the reagent fluids usually needs to be constant and at a low level.

Cooling units comprising a Peltier element as a cooling element are often used to cool reagent compartments in smaller medical instruments. The cold side of the cooling element is usually attached to the reagent compartment cooling the inside of the reagent compartment. The warm side of the cooling element needs to be cooled with forced air flow. Peltier elements are bolted to the reagent compartment and to the heat exchanger with tightly controlled torque.

The space above the reagent compartment usually has to be accessed by a pipettor, so that the cooling units cannot be mounted above the reagent compartment. The front of the reagent compartment must be accessible to load reagents or reagent racks into the reagent compartment so that the cooling unit cannot be mounted at the front.

Cooling units are therefore usually attached to the bottom or to the rear of the reagent compartment. The reagent compartment then needs to be made from heat conductive materials in order to distribute the temperature.

Cooling units mounted to the bottom of the reagent compartment have the cold side of the cooling element above the warm side of the cooling element. Complex insulation is thereby necessary, which also needs to be watertight because condensed water on the cold side of the cooling element can drip onto the warm side of the cooling element and spoil the electric contacts of the cooling element. Precautions have to be taken to prevent any liquids, spilled or condensed, to enter the cooling units.

If the cooling units are mounted to the bottom of the reagent compartment, the cooling units add to the overall height of the system comprising the device for cooling the reagent compartment and the reagent compartment, because of the heat exchanger and the space for forced air flow at the bottom of the reagent compartment.

Service access to the cooling units is usually only possible if the entire device for cooling a reagent compartment is removed and the cooling units are detached from the reagent compartment.

SUMMARY OF THE INVENTION

It is thus an object of the present invention to provide a device, system and method for cooling a reagent compartment, wherein the device separates the cooling unit from the reagent compartment leading to more freedom regarding the shape and material of the cooled reagent compartment. Access to the cooling unit shall also be improved compared to traditional direct cooling.

The instant disclosure provides a cooling device for attachment to a reagent compartment within an automated analyser system, comprising a housing with a first side for attachment to the reagent compartment, a cooling unit with at least one cooling element with a warm upper side and a cold lower side, that is equipped with a cold side heat exchanger comprising at least one first fan, a at least one cold air channel and at least one cold air opening at the first side of the housing for circulating cold air between the at least one cooling element and the reagent compartment in a closed system.

The at least one first fan can be arranged within the at least one cold air channel between the at least one cold air outlet and the cold lower side of the cooling element.

The device may further comprise at the first side of the housing at least one warm air inlet channel arranged below and separated from the at least one cold air channel for taking up warm air from the compartment and guiding it to the cold lower side of the at least one cooling element.

It is also intended that the device may further comprise g a warm heat exchanger comprising at least one second fan and at least one warm air channel arranged between the warm upper side of the at least one cooling element and at least one warm air opening at a second side of the housing At least one ambient air channel can be arranged between at least one opening within a third side of the housing and the warm upper side of the cooling element for cooling down the warm upper side of the at least one cooling element.

It is envisaged that the warm upper side and cold lower side of the at least one cooling element are separated by an insulation from each other.

The at least one cooling element may be a Peltier element, wherein a spacer may serve to separate the warm upper side and cool lower side of the at least one cooling element.

A temperature sensor can be integrated into the spacer.

It is intended that a spring can connect the warm upper side and the cold lower side of the at least one cooling element.

The at least one cooling element may be shaped in manner ensuring the correct orientation with a warm upper side and a cold lower side of the at least one cooling element.

Another object of the instant invention is a system for cooling a reagent compartment comprising a device for cooling a reagent compartment comprising a housing with a first side for attachment to the reagent compartment, a cooling unit with at least one cooling element with a warm upper side and a cold lower side, that is equipped with a cold side heat exchanger comprising at least one first fan, a at least one cold air channel and at least one cold air opening at the first side of the housing for circulating cold air between the at least one cooling element and the reagent compartment in a closed system.

A further object of the instant invention is a method for cooling a reagent compartment, wherein the method comprises the steps of:

a. providing a device for cooling a reagent compartment comprising
  i. a housing with a first side for attachment to the reagent compartment, a cooling unit with at least one cooling element with a warm upper side and a cold lower side, that is equipped with a cold side heat exchanger comprising at least one first fan, a at least one cold air channel and at least one cold air opening at the first side of the housing for circulating cold air between the at least one cooling element and the reagent compartment in a closed system;

ii. at the first side of the housing at least one warm air inlet channel arranged below and separated from the at least one cold air channel for taking up warm air from the compartment and guiding it to the cold lower side of the at least one cooling element;

b. running the at least one fan for warm air circulation and the at least one fan for cold air circulation, so that cold air circulates from the cold lower side of the at least one cooling element into the reagent compartment and the warm air coming from the compartment is circulated to the cold lower side of the at least one cooling element.

Finally, a use of a cooling device mounted to a reagent compartment for cooling the reagent compartment is an object of the instant invention, the device comprising a housing with a first side for attachment to the reagent compartment, a cooling unit with at least one cooling element with a warm upper side and a cold lower side, that is equipped with a cold side heat exchanger comprising at least one first fan, a at least one cold air channel and at least one cold air opening at the first side of the housing for circulating cold air between the at least one cooling element and the reagent compartment in a closed system and at the first side of the housing at least one warm air inlet channel arranged below and separated from the at least one cold air channel for taking up warm air from the compartment and guiding it to the cold lower side of the at least one cooling element.

SUMMARY OF THE FIGURES

The invention will now be described on the basis of the drawings. It will be understood that the embodiments and aspects of the invention described herein are only examples and do not limit the protective scope of the claims in any way. The invention is defined by the claims and their equivalents. It will be understood that features of one aspect or embodiment of the invention can be combined with a feature of a different aspect or aspects and/or embodiments of the invention. It shows:

DETAILED DESCRIPTION OF THE INVENTION

The invention relates to a device for cooling a reagent compartment comprising a housing with a first side for attachment to the reagent compartment and a second side away from the reagent compartment, a cooling unit with a cooling element with an upper warm side and a lower cold side, a warm heat exchanger above the cooling element and a cold heat exchanger below the cooling element, a cold air outlet and a warm air inlet, a fan for warm air circulation for cooling down the upper warm side of the cooling element and a fan for cold air circulation between cold heat exchanger and reagent compartment for cooling down the reagent compartment.

Figure 1:
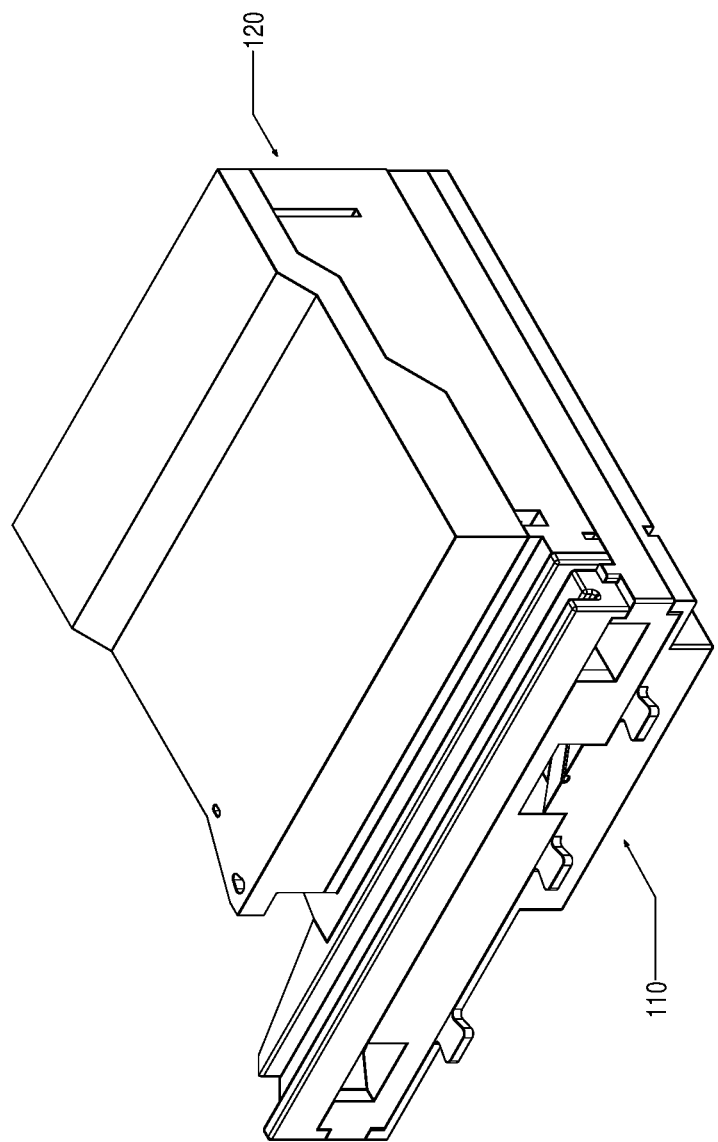
FIG. 1 is a perspective view of a device of an embodiment of the present invention.

FIG. 1 shows a top/side view of a device of the present invention. The device comprises a first side of the housing 110 for attachment to the reagent compartment and a second side of the housing 120 away from the reagent compartment.

The second side of the housing away from the reagent compartment may be opposite the first side of the housing for maximal distance between first side of the housing and second side of the housing. This setup is advantageous because the second side of the housing may be equipped with fans for warm air circulation and the cooling unit may be assembled close to the second side of the housing so that the cooling unit is maximally separated from the reagent compartment.

Figure 2:
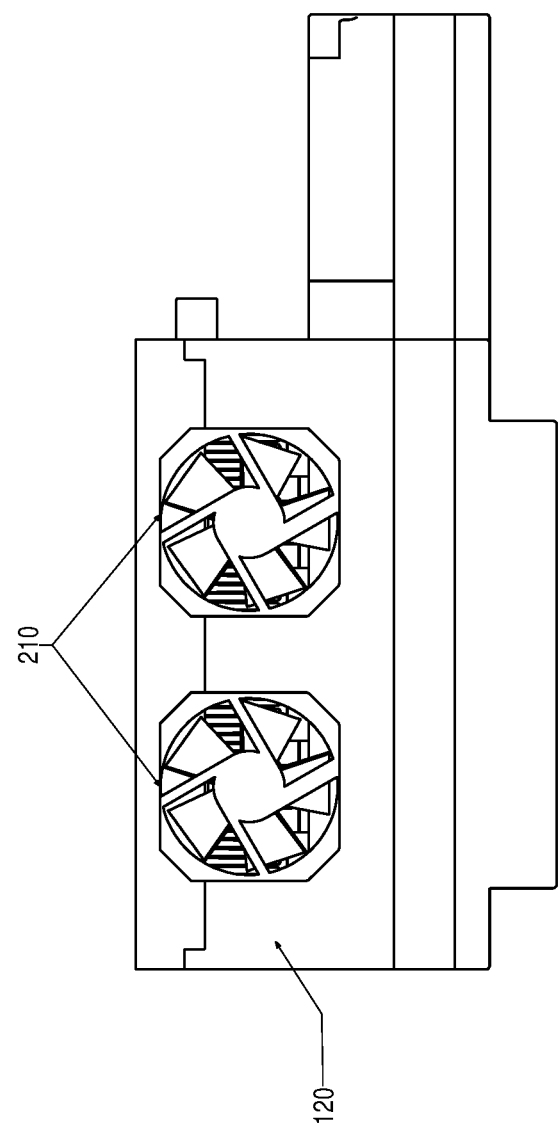
FIG. 2 is a rear view of a device of an embodiment of the present invention.

FIG. 2 shows a rear view of a device. Fans for warm air circulation 210 are depicted at the second side of the housing 120.

Figure 3:
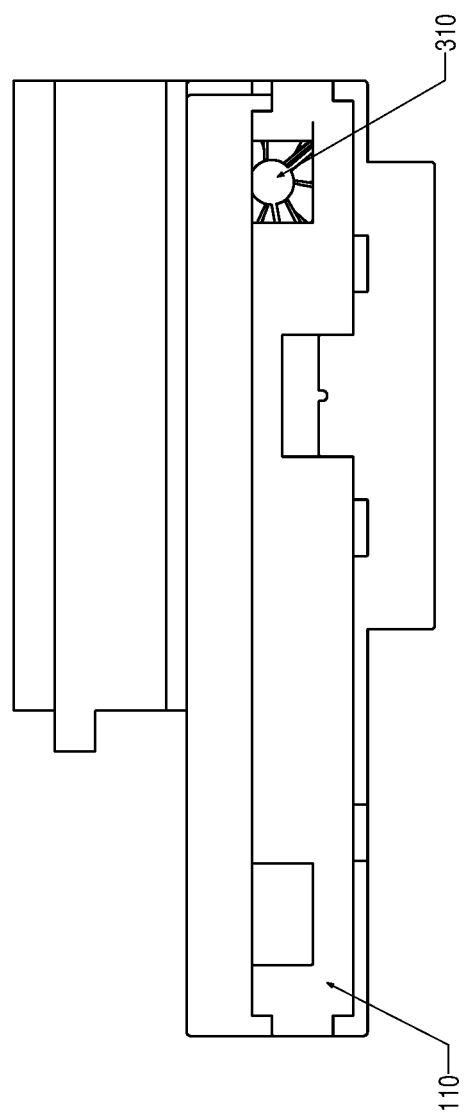
FIG. 3 is a front view of a device of an embodiment of the present invention.

In FIG. 3, the front view of a device is shown. A fan for cold air circulation 310 at the first side of the housing 110 is depicted.

Figure 4:
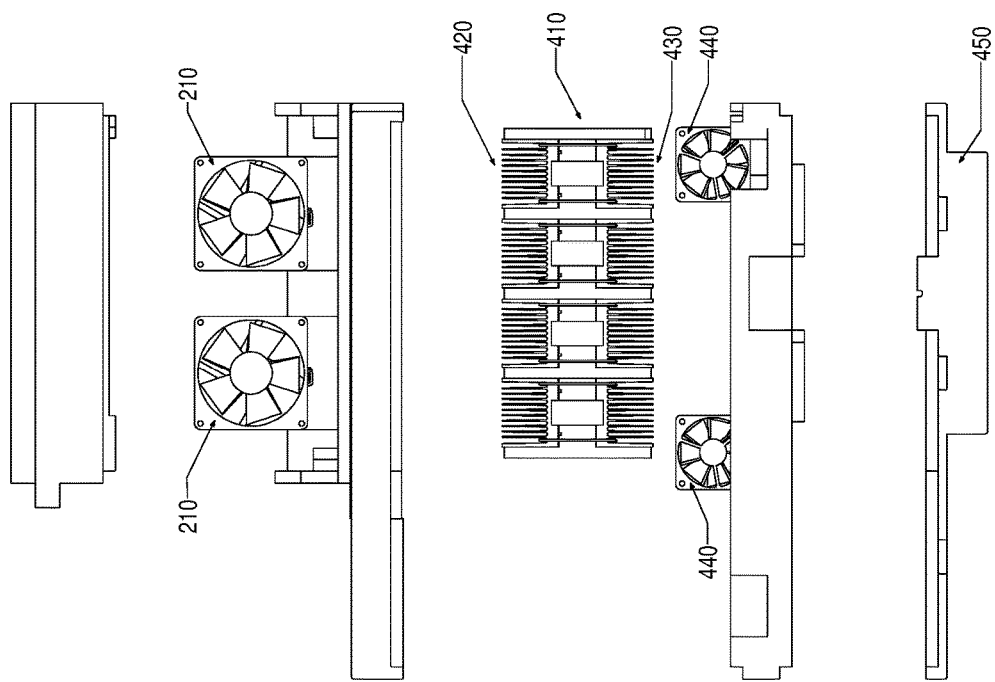
FIG. 4 is a front view of an exemplary set-up of a device of an embodiment of the present invention.

FIG. 4 illustrates an exemplary setup of a device (front view). The setup is spread vertically for better visualization. The device comprises fans for warm air circulation 210, a cooling unit 410 comprising a warm heat exchanger 420 and a cold heat exchanger 430, and fans for cold air circulation 440. The housing comprises all components and serves for keeping the components together. A bottom insulation 450 comprises air channels for air flow. The device may comprise several cooling units 410.

Figure 5:
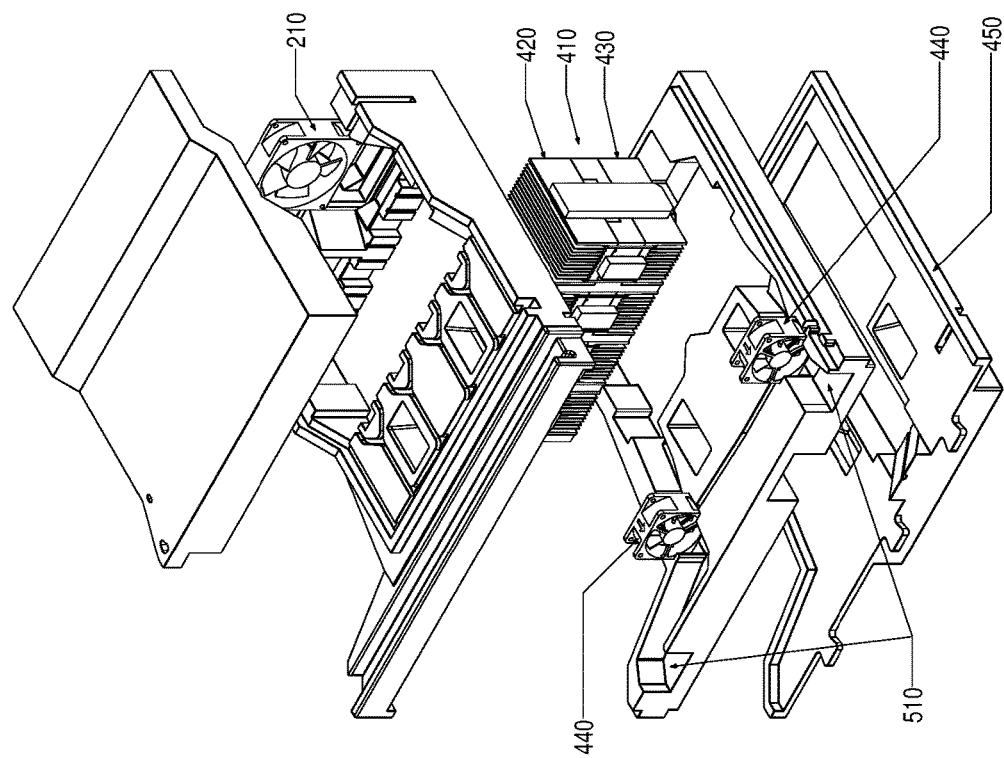
FIG. 5 is an assembly view of an exemplary setup of a device of an embodiment of the present invention.

FIG. 5 shows a top view of an exemplary setup of a device. The fan for cold air circulation 440 and the cold air outlet 510 are arranged closer to the first side of the housing than the cooling unit 410 comprising a warm heat exchanger 420 and a cold heat exchanger 430 in order to separate the cooling unit from the reagent compartment.

The cooling unit 410 and the fan for warm air circulation 210 are arranged closer to the second side of the housing than the fan for cold air circulation 440 and the cold air outlet 510, also in order to separate the cooling unit from the reagent compartment.

The fan for warm air circulation serves for cooling down the upper warm side of the cooling element and the fan for cold air circulation between cold heat exchanger and reagent compartment serves for cooling down the reagent compartment.

Figure 6:
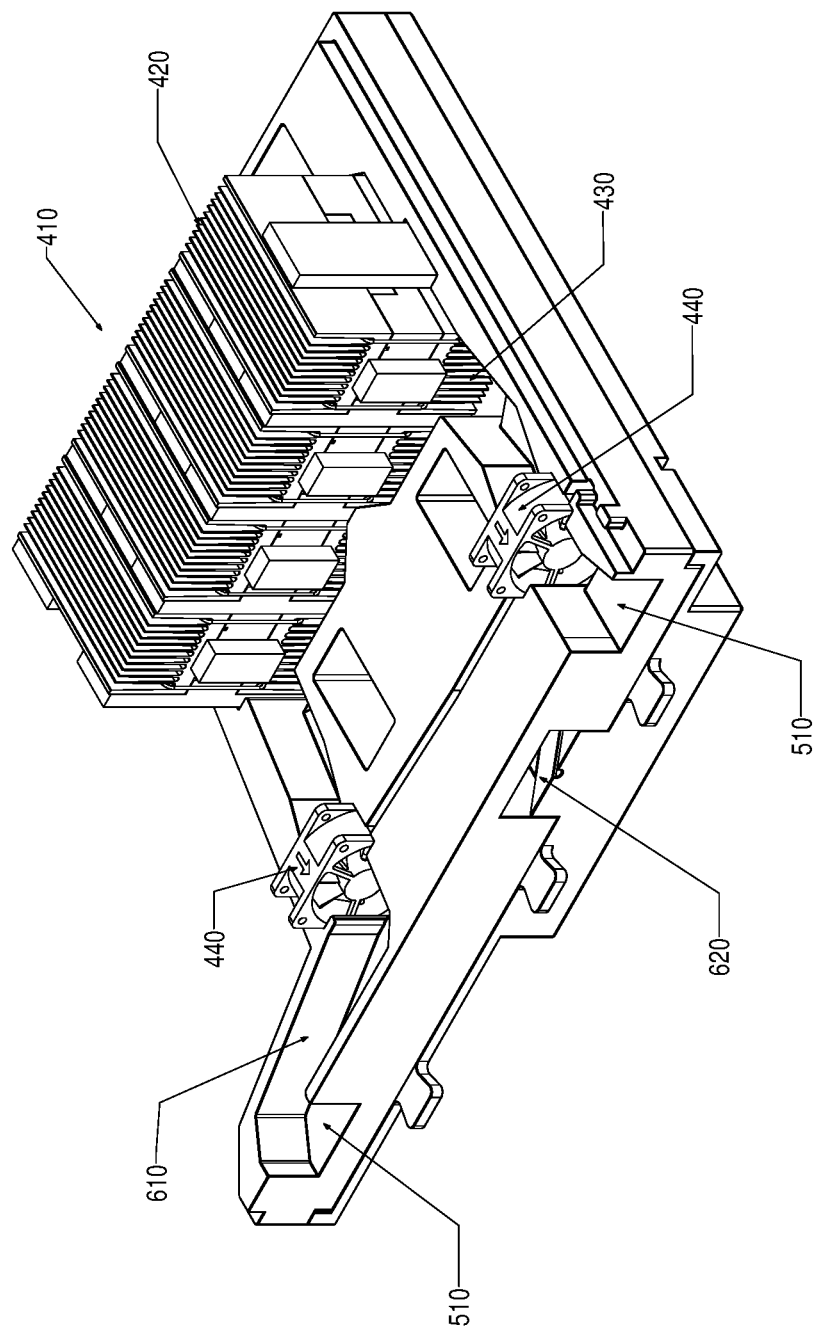
FIG. 6 is a perspective view of a housing with a cooling unit and fans for cold air circulation of an embodiment of the present invention.

FIG. 6 illustrates the top/side view of a housing with a cooling unit and fans for cold air circulation, showing the inside of a device. A cooling unit 410 comprising a warm heat exchanger 420 and a cold heat exchanger 430 is mounted away from the fans for cold air circulation 440. The cold air outlet 510 which guides the cold air from the fan for cold air circulation 440 through an air channel 610 to a reagent compartment is also shown. Warm air from a reagent compartment enters the device via a warm air inlet 620.

Figure 7:
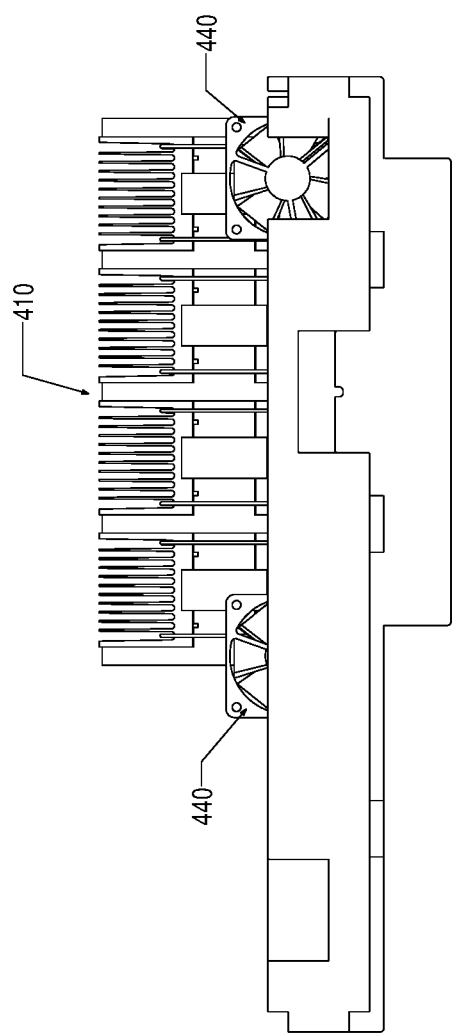
FIG. 7 is a front view of the housing of FIG. 6.

A front view of the housing of FIG. 6 is shown in FIG. 7. A cooling unit 410 and fans for cold air circulation 440 are mounted inside the housing.

Figure 8:
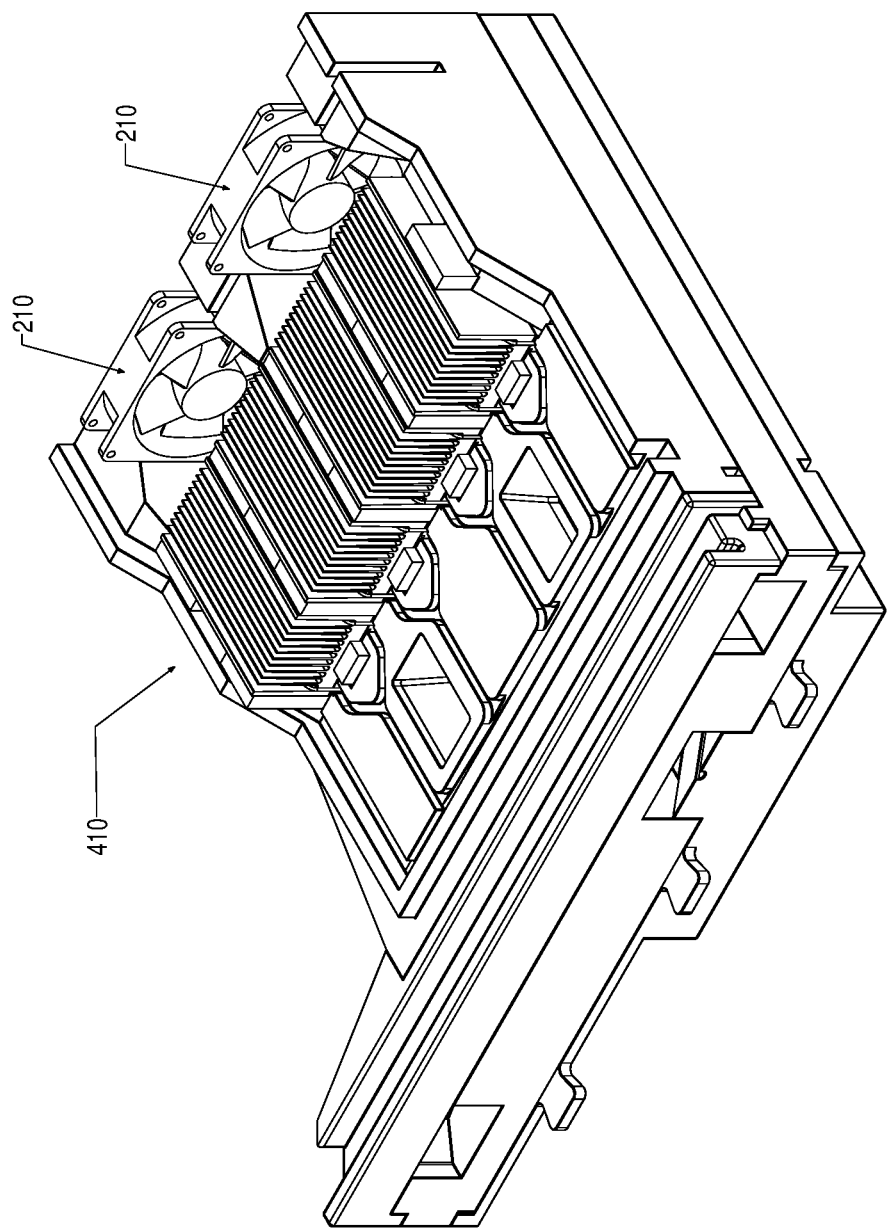
FIG. 8 is a top/side perspective view of a housing with a cooling unit and fans for warm air circulation of an embodiment of the present invention.
Figure 9:
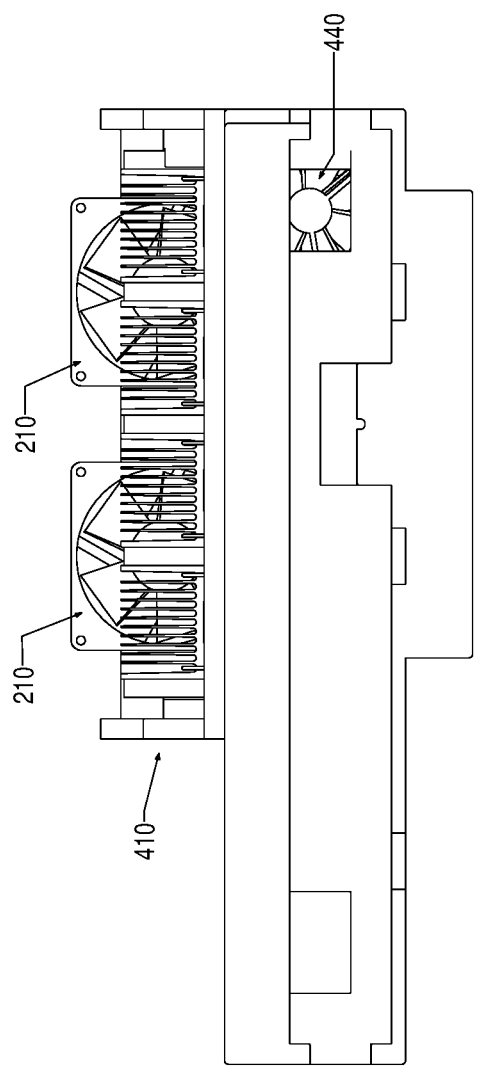
FIG. 9 is a front view of the housing of FIG. 8.

FIG. 8 illustrates the top/side view of a housing with a cooling unit and fans for warm air circulation, showing the inside of a device. A cooling unit 410 is mounted close to the fans for warm air circulation 210. FIG. 9 shows the front view of the housing of FIG. 8 comprising a fan for cold air circulation 440, a cooling unit 410 and fans for warm air circulation 210.

Figure 10:
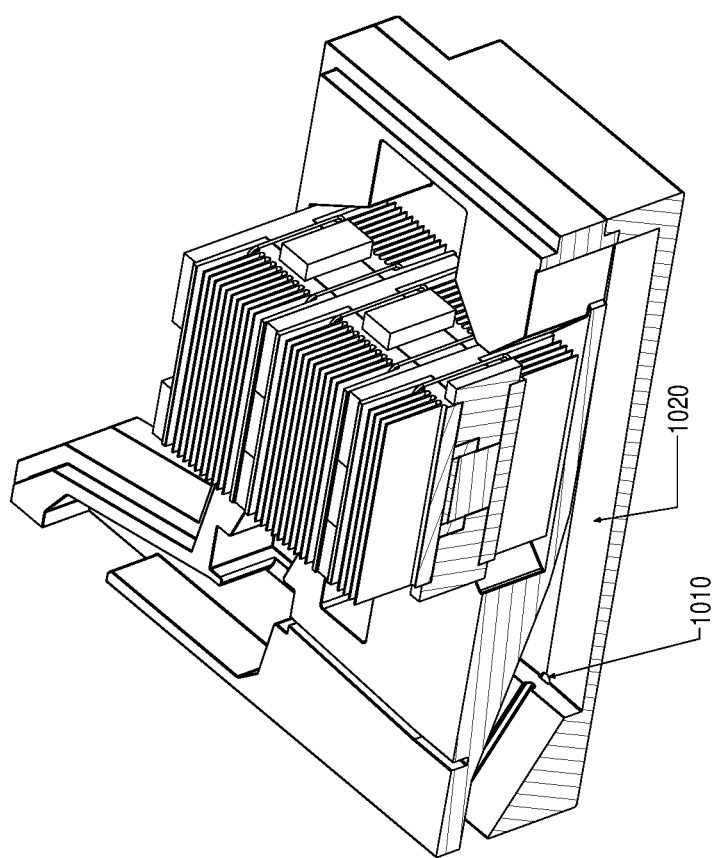
FIG. 10 is a housing of an embodiment of the present invention comprising a hole and slope.

The housing may also comprise a hole 1010 to drain condensed water or a slope 1020 to lead condensed water, as shown in FIG. 10. Condensed water may build up on the cold side of the cooling element. The inventive device allows draining of the condensed water and avoids that the warm side of the cooling element is affected by condensed water because the cooling element has an upper warm side and a lower cold side, meaning that the warm side is arranged above the cold side. Since the condensed water is naturally lead downwards, the condensed water cannot harm the warm side of the cooling element.

The cooling units comprise a cooling element with an upper warm side and a lower cold side, a warm heat exchanger above the cooling element and a cold heat exchanger below the cooling element. The units are equipped with a connector for cooling element power. The entire cooling unit can be replaced easily by opening the housing of the device, detaching the connector and replacing the cooling units with a new one. The shape of the housing enforces correct insertion of a new unit.

The housing also serves the purpose of insulation. The housing may also be an insulated block.

One embodiment of the present invention comprises a device for cooling, wherein the cold heat exchanger is coupled to the cold side of the cooling element with a spacer for separating the cold heat exchanger from the cold side of the cooling element. A temperature sensor may be integrated in the spacer. The measurements of the temperature sensor can be used for temperature control and to prevent ice build up on the cold side of the cooling element.

In another embodiment, the warm heat exchanger may be directly coupled to the warm side of the cooling element for heat exchange. A spring may connect the warm heat exchanger and the cold heat exchanger for generating a contact force between warm heat exchanger, cooling element and cold heat exchanger.

Figure 11:
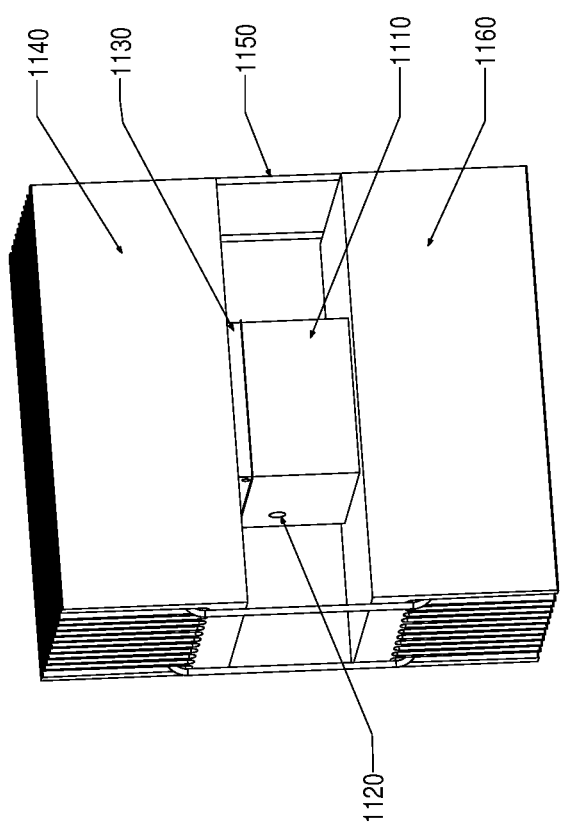
FIG. 11 is a view of a cooling unit comprising a spacer in an embodiment of the present invention.

FIG. 11 shows a cooling unit comprising a spacer. The spacer 1110 comprises a mounting hole 1120 to install a temperature sensor. The cooling element 1130 is directly mounted with the upper warm side of the cooling element to the warm heat exchanger 1140. Springs 1150 lower the risk of damage caused by the temperature difference between the cold side and the warm side. The cold heat exchanger 1160 is not directly coupled to the cold side of the cooling element 1130, but via a spacer 1110.

The cooling element may be a Peltier element.

Figure 12:
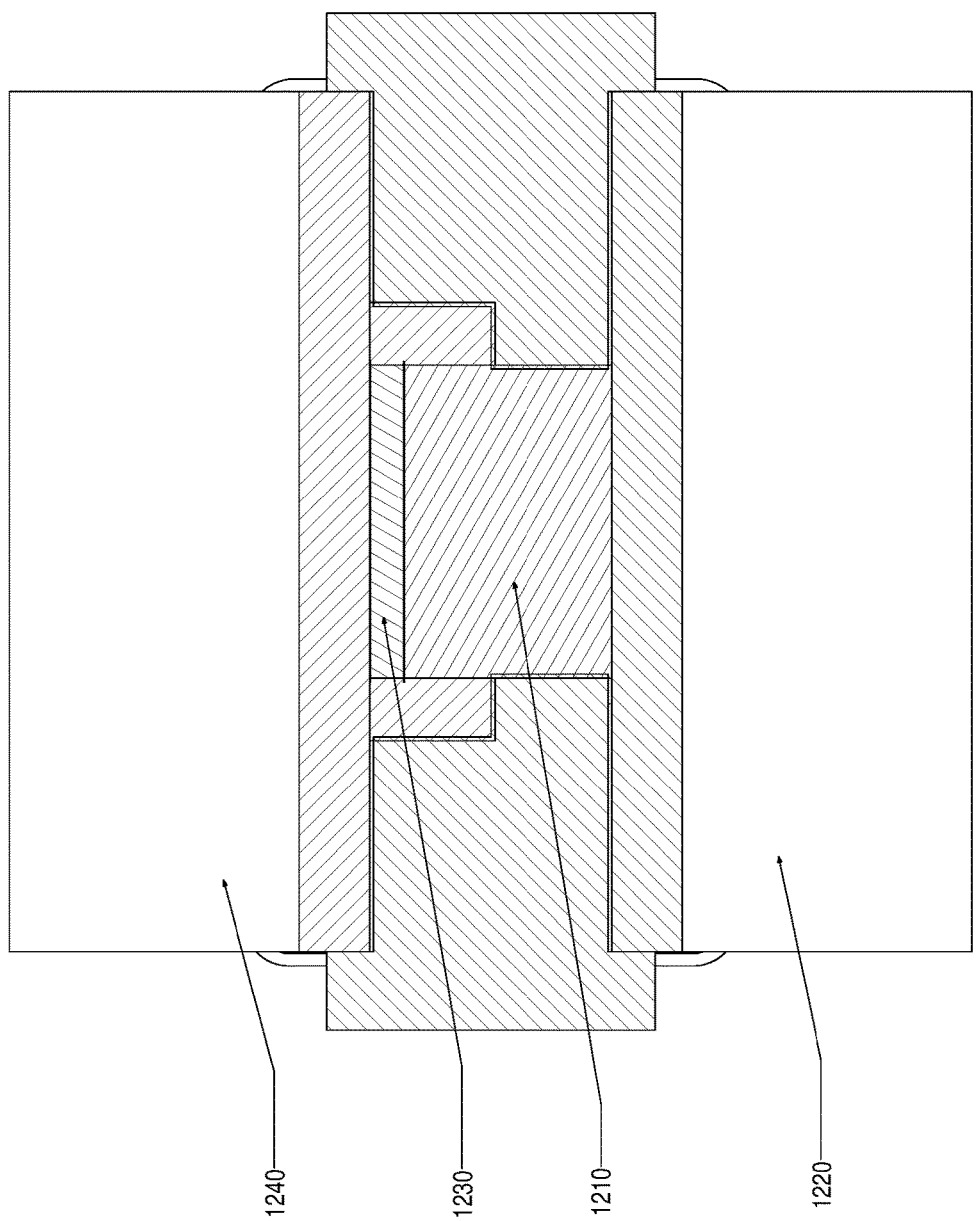
FIG. 12 is a side view of a cooling unit and a cooling element of an embodiment of the present invention.

FIG. 12 shows a side view of a cooling unit and a cooling element. A spacer 1210 separates a cold heat exchanger 1220 from a cooling element 1230, which is directly coupled to the warm heat exchanger 1240.

Figure 13:
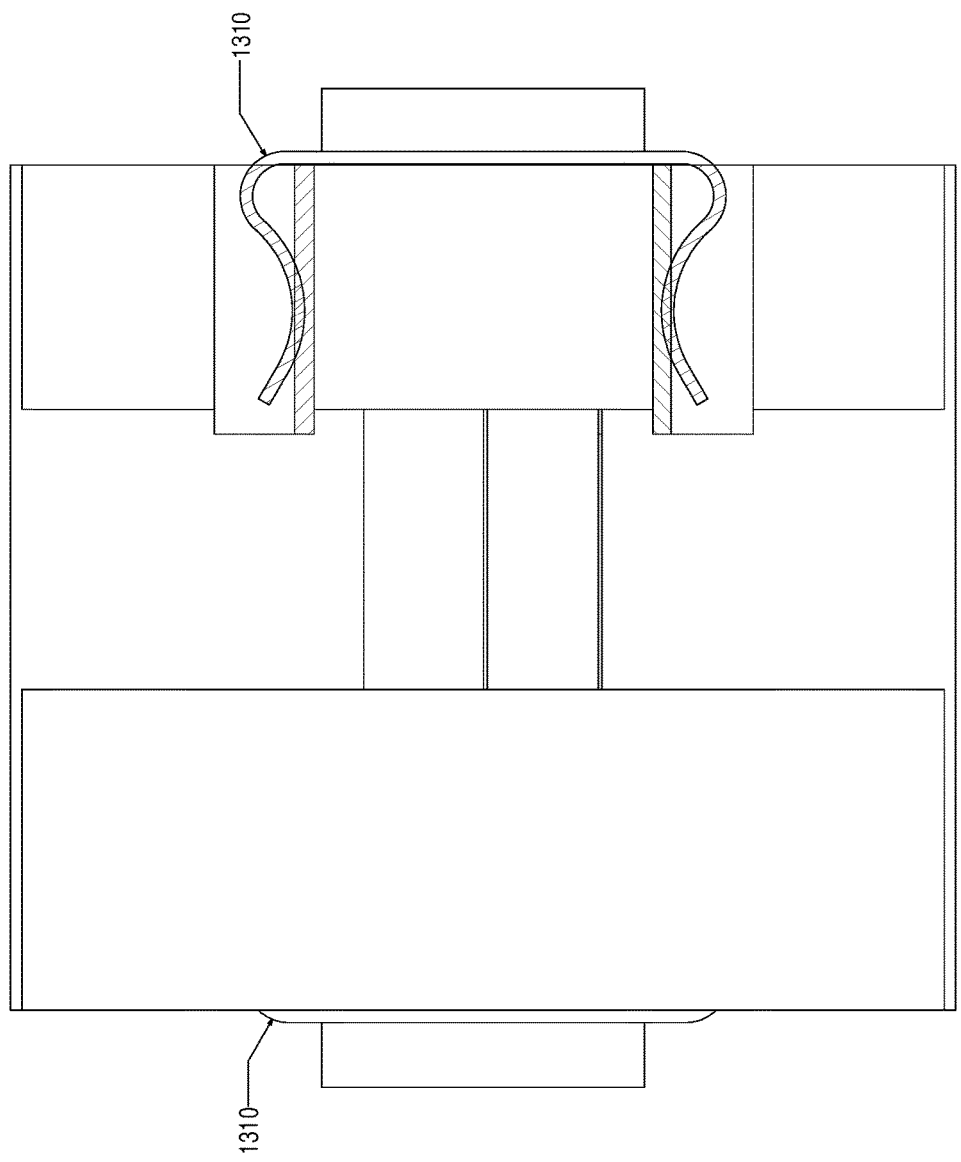
FIG. 13 is a side view of a cooling unit of an embodiment of the present invention.

A side view of a cooling unit is also shown in FIG. 13. It is exemplified how the springs 1310 connect the warm heat exchanger and the cold heat exchanger.

Figure 14:
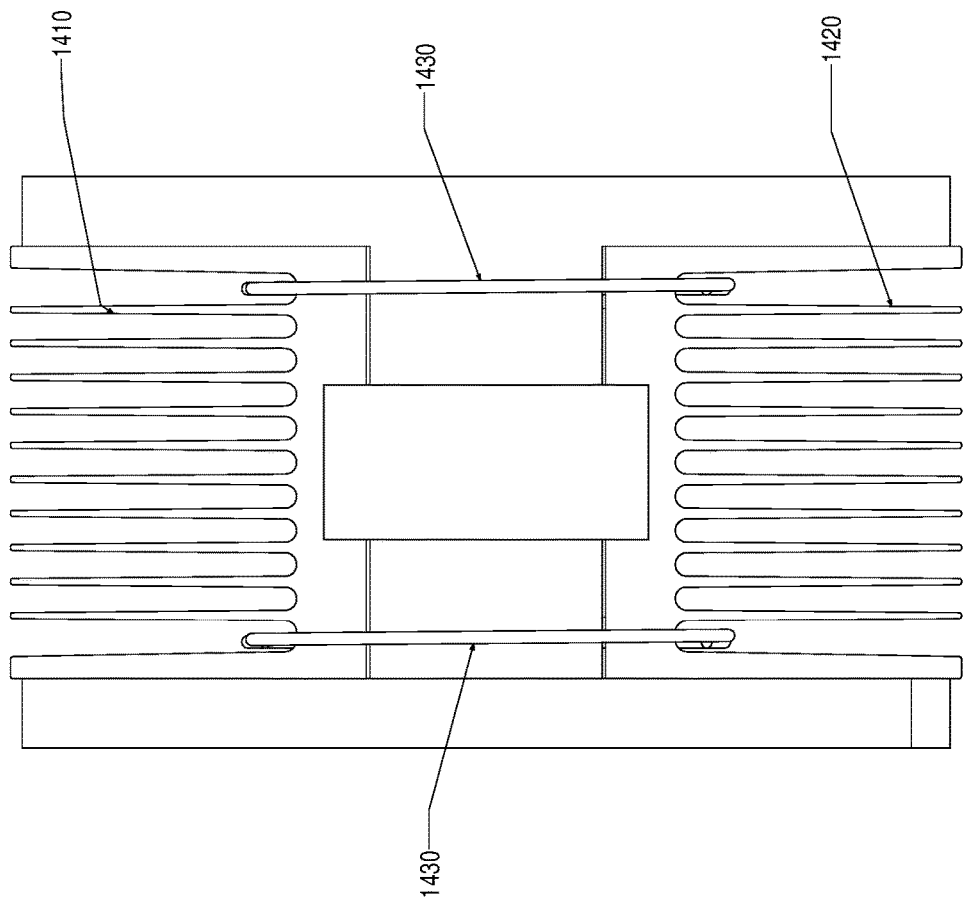
FIG. 14 is a rear view of a cooling unit of an embodiment of the present invention.

The rear view of a cooling unit is shown in FIG. 14. In this view, the warm heat exchanger 1410 and the cold heat exchanger 1420, which are connected by springs 1430 are shown in more detail.

The device may also comprise a heat pipe between the cooling element and the warm heat exchanger to transfer heat. The heat may be transferred to a suitable part of the device.

Figure 15:
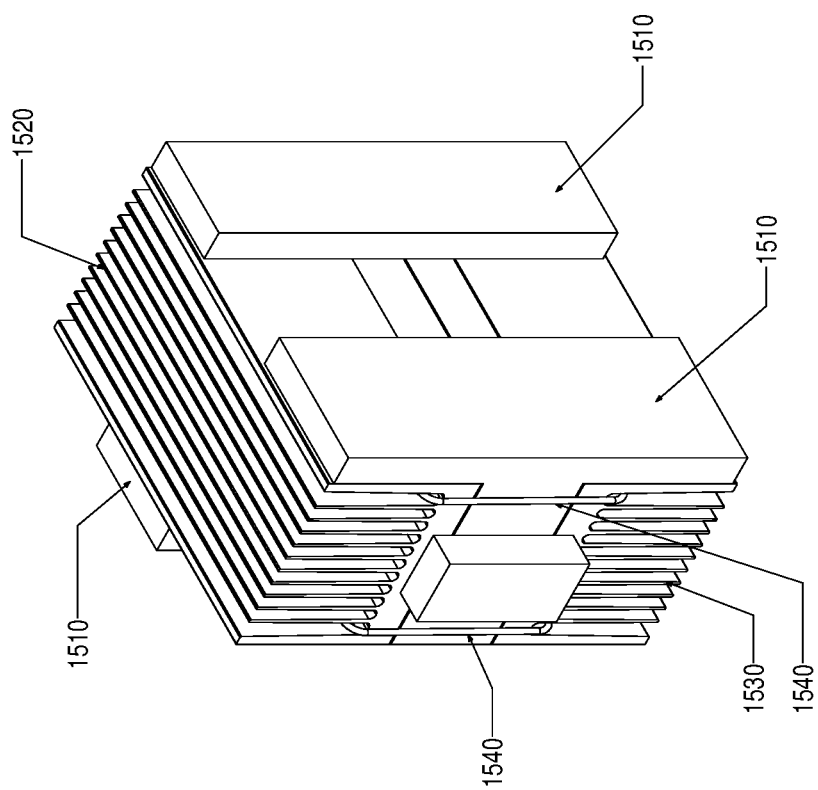
FIG. 15 is a view of a cooling unit comprising an insulation of an embodiment of the present invention.

In one embodiment, the cooling unit comprises an insulation attached to the warm heat exchanger and the cold heat exchanger and separating the warm heat exchanger and the cold heat exchanger from each other. FIG. 15 shows a cooling unit comprising an insulation. The insulation 1510 is attached to the warm heat exchanger 1520 and the cold heat exchanger 1530. Springs 1540 generate the appropriate contact force between warm heat exchanger 1520, cold heat exchanger 1530 and cooling element.

Figure 16:
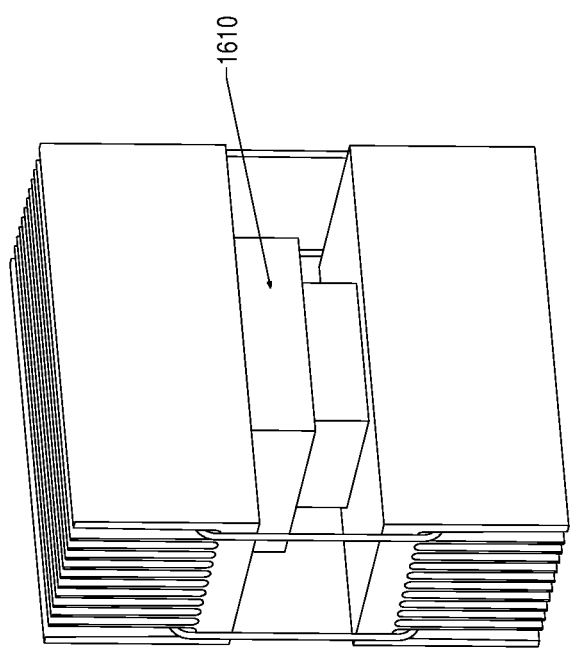
FIG. 16 is a view of insulation surrounding a cooling element of an embodiment of the present invention.

The cooling unit may also comprise an insulation surrounding the cooling element. Such an insulation 1610 surrounding a cooling element is shown in FIG. 16.

Insulation generally serves the purpose of reducing heat transfer. The device of the present invention may comprise insulation in the housing, and the device may also comprise insulation comprised in the cooling unit. Insulation may be added wherever heat transfer is to be reduced or avoided.

Figure 17A:
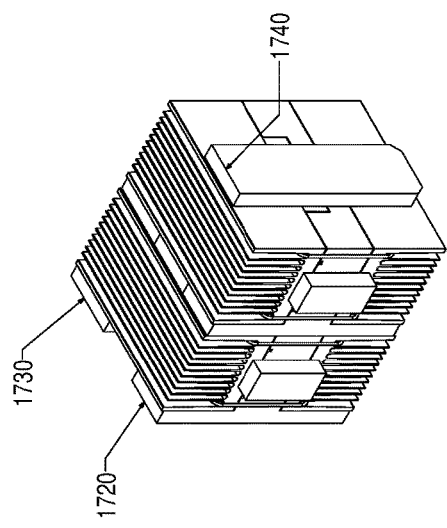
FIGS. 17A, 17B and 17C illustrate two cooling units of an embodiment of the present invention.
Figure 17C:
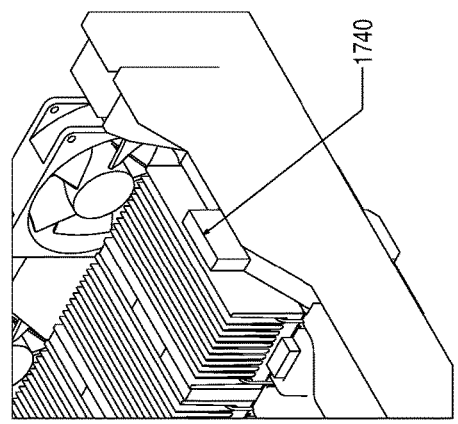
Figure 17B:
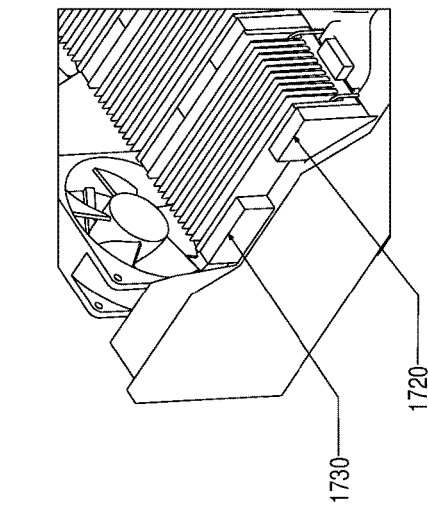

The shape of the insulation comprised in the cooling unit and the shape of the housing may ensure correct insertion of the cooling unit in the housing. FIG. 17 shows two cooling units 1710. The two insulation parts 1720 and 1730 on the left hand side of FIG. 17A have different widths. Another insulation part is shown as 1740. The width of insulation 1720 is smaller than the width of insulation 1730. FIGS. 17B and 17C illustrate how the housing is adapted to accommodate the cooling units so that wrong insertion of the cooling units is prevented.

The control unit of the cooling unit may measure the Seebeck voltage of the individual cooling elements. This would enable to get information about the correct functionality and performance of the cooling units.

The present invention also provides a system for cooling a reagent compartment, wherein the system comprises the device of the present invention and a reagent compartment.

Figure 18A:
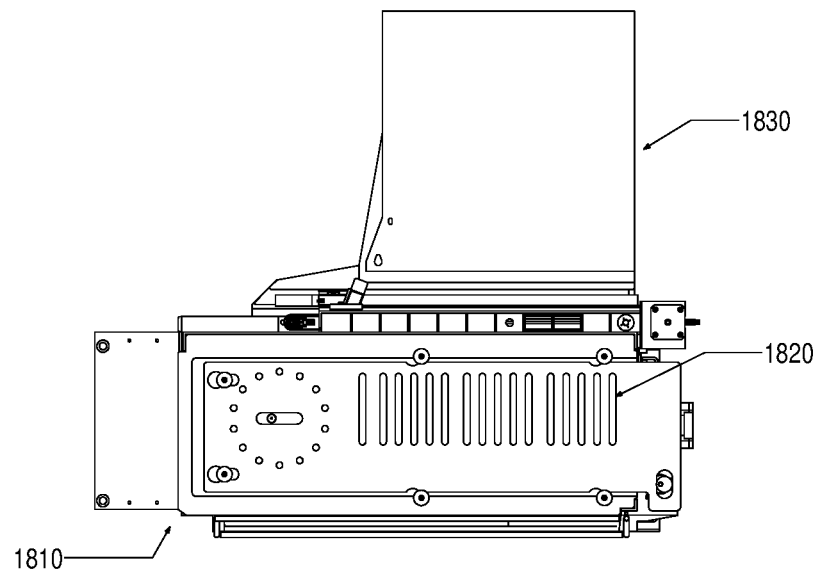
FIGS. 18A and 18B are a top view and front view of a system of the present invention.
Figure 18B:
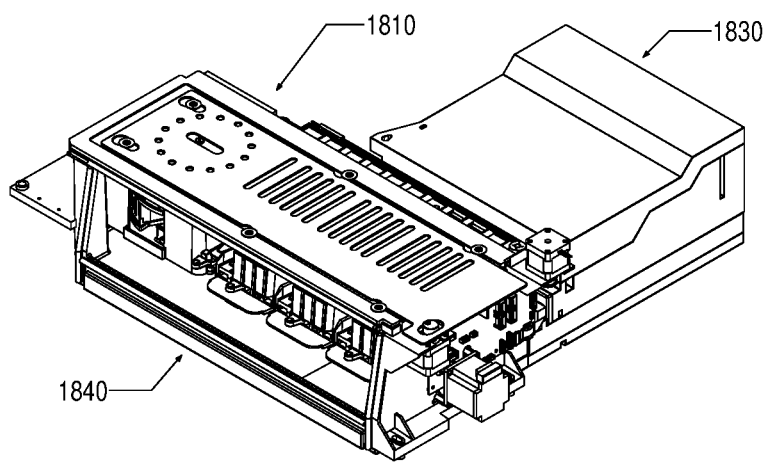

FIG. 18 shows a tops view (18A) and a front view (18B) of a system of the present invention. The reagent compartment 1810 comprises lanes 1820 for the insertion of reagent racks. The device, shown as 1830, is mounted behind the reagent compartment 1810, leading to more freedom regarding the shape and material of the cooled reagent compartment. The reagent compartment 1810 in FIG. 18 does not have a front door. The front opening 1840 in FIG. 18B allows user access and rack insertion. Therefore, the device for cooling the reagent compartment cannot be mounted in front of the reagent compartment.

The housing may thus be formed so that the housing accepts cooling elements with heat exchangers (warm heat exchanger and cold heat exchanger) on each side. The cold heat exchanger may be coupled to the cooling element with a spacer out of heat conductive material. The warm heat exchangers may be coupled to the cooling element directly for best heat transfer. An insulation may separate warm side from cold side of the cooling element.

Fans for both warm air circulation as well as cold air circulation are integrated into the housing. The housing is adapted to form the air channels for cold side and warm side air flow.

A method for cooling a reagent compartment is thus provided, wherein the method comprises the following steps:
 a. providing the device of the present invention,
 b. running the fan for warm air circulation and the fan for cold air circulation, so that cold air circulates from the cold heat exchanger through the fan for cold air circulation and the cold air outlet to the reagent compartment, and warm air circulates from the reagent compartment through the warm air inlet to the cold heat exchanger, and ambient air circulates from a bottom of the device through the warm heat exchanger and through the fan for warm air circulation.

Figure 19A:
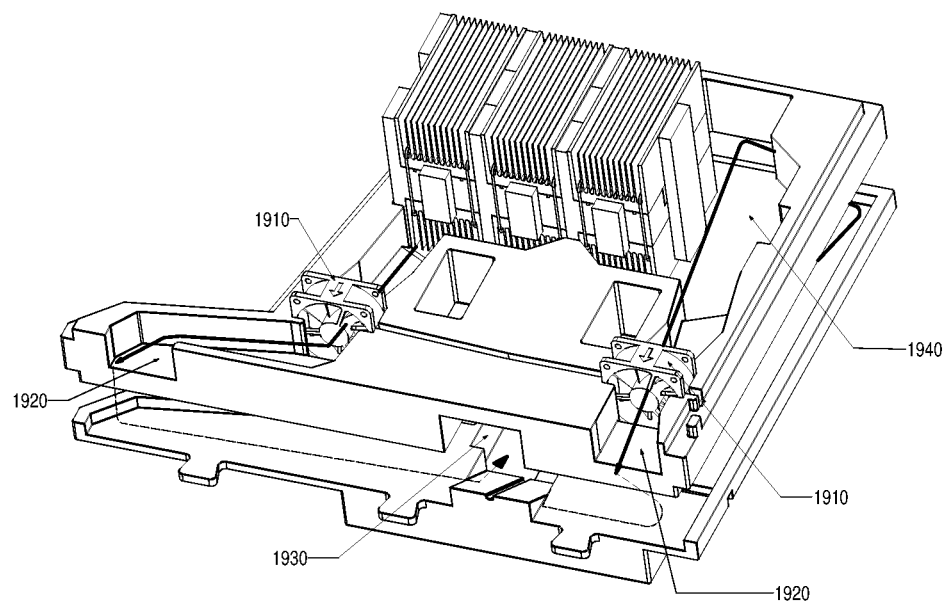
FIGS. 19A, 19B and 19C are top and side views of the device and the air flow through the fans for cold air circulation.
Figure 19B:
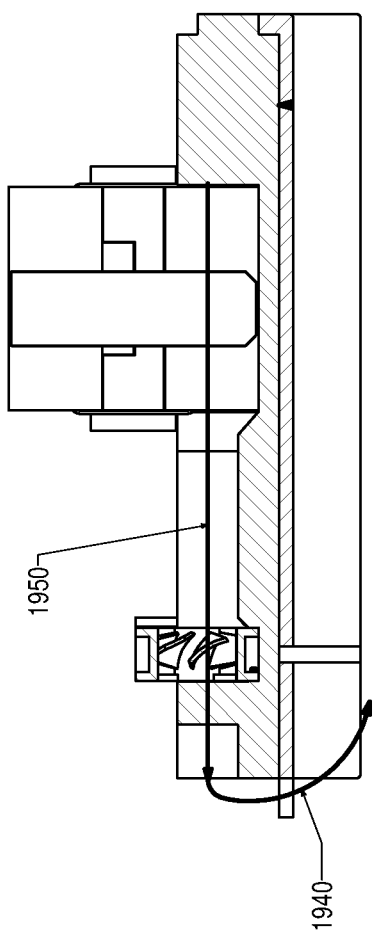
Figure 19:
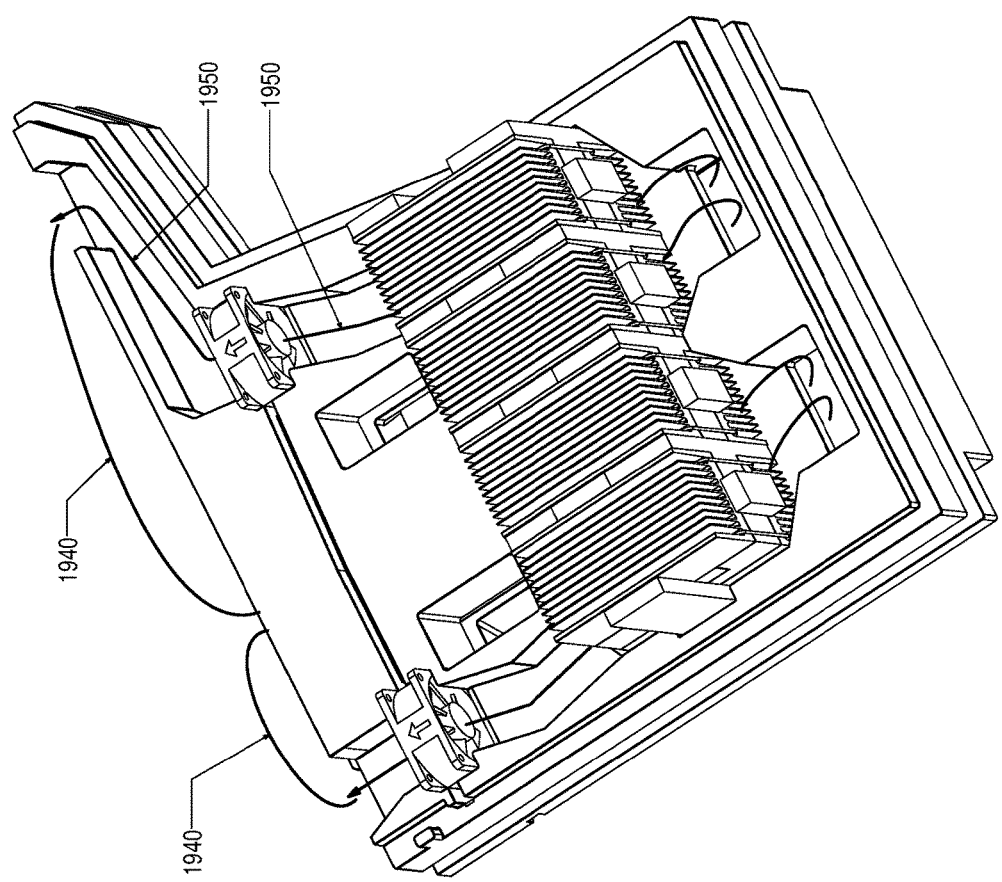

FIG. 19 illustrates a top/side view of the device and the air flow through the fans for cold air circulation. The fans for cold air circulation 1910 initiate air flow in FIG. 19A. Cold air exits the device via the cold air outlet 1920 to the reagent compartment. The air flow thus lowers the internal temperature of the reagent compartment. The air flows back through the warm air inlet 1930 into the device. Warm air 1940 comes up to the cooling element to be cooled down again. The cold air circulation is further shown in FIGS. 19B and 19C. The air flow of warm air 1940 and cold air 1950 is shown.

Figure 20A:
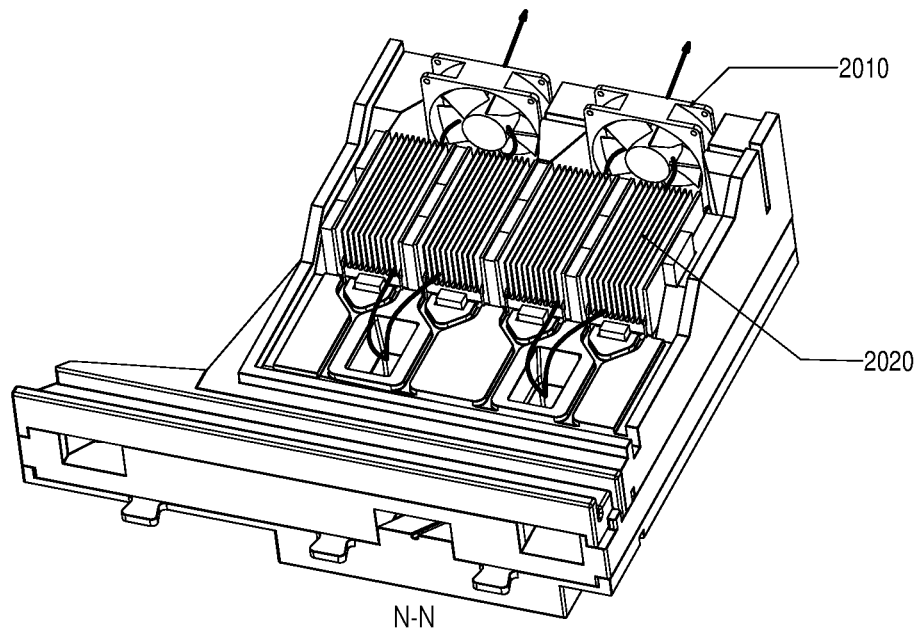
FIGS. 20A and 20B illustrate air flow through the fans for warm air circulation of an embodiment of the present invention.
Figure 20B:
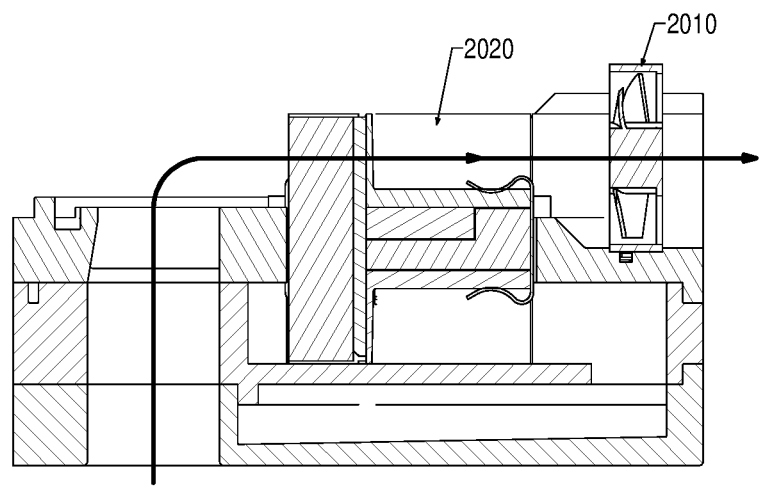

FIG. 20 shows the air flow through the fans for warm air circulation (20A: top view; 20B: side view). Fans for warm air circulation 2010 aspirate ambient air 2020. Ambient air 2020 then circulates from a bottom of the device through the warm heat exchanger and through the fan for warm air circulation 2010. Ambient air 2020 cools down the warm side of the cooling element to increase the cooling effect. The ambient air 2020 warms up when passing the warm side of the cooling element.

Figure 21:
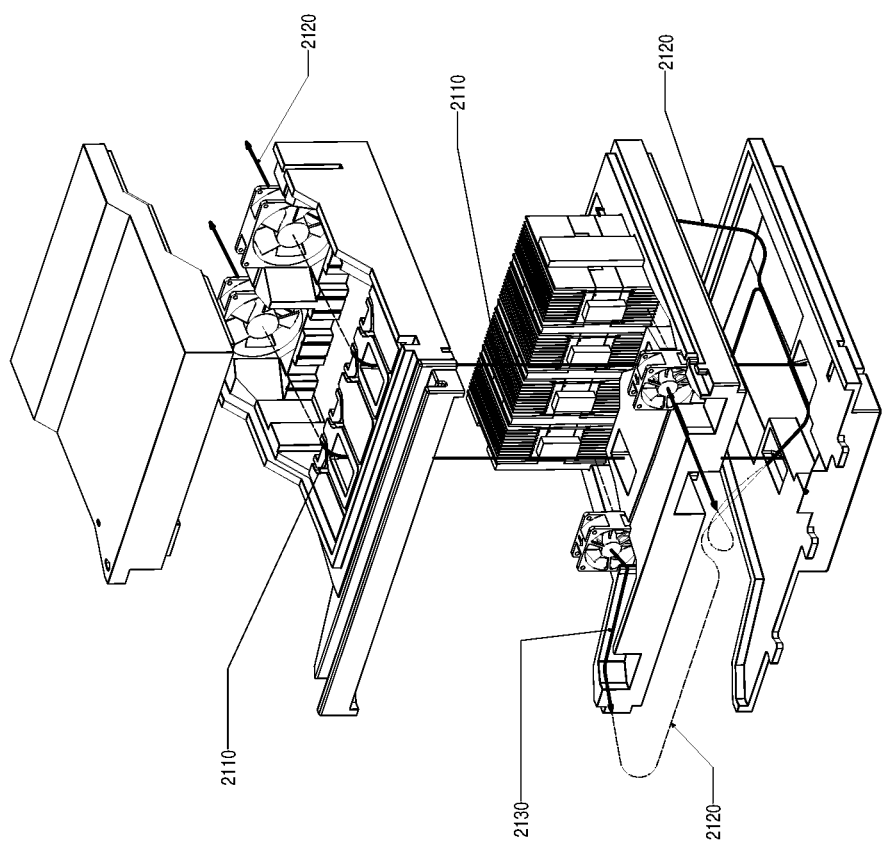
FIG. 21 shows a complete air flow of an embodiment of the present invention.

The complete air flow is shown in FIG. 21. Ambient air 2110 circulates from the bottom of the device through the warm heat exchanger and as warm air 2120 through the fan for warm air circulation. Cold air 2130 circulates from the cold heat exchanger through the fan for cold air circulation and the cold air outlet to the reagent compartment, and warm air 2120 circulates from the reagent compartment through the warm air inlet to the cold heat exchanger.

In the new device, the cooling units are separated from the reagent compartment and are mounted "upside down" compared with the state of the art. The warm side of the cooling element is above the cold side of the cooling element, and the cold side of the cooling element as well as the warm side of the cooling element is equipped with a cold heat exchanger and a warm heat exchanger, respectively. A fan for cold air circulation is circulating air between the cold heat exchanger and the reagent compartment in a closed system. The warm side of the cooling element is cooled with an open air flow.

Use of the device of the present invention for cooling a reagent compartment is also provided.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

LIST OF REFERENCE NUMERALS

110 first side of the housing
120 second side of the housing
210 fans for warm air circulation
310 fan for cold air circulation
410 cooling unit
420 warm heat exchanger
430 cold heat exchanger
440 fan for cold air circulation
450 bottom insulation
510 cold air outlet
610 air channel
620 warm air inlet
1010 hole
1020 slope
1110 spacer
1120 mounting hole
1130 cooling element
1140 warm heat exchanger
1150 springs
1160 cold heat exchanger
1210 spacer
1220 cold heat exchanger
1230 cooling element
1240 warm heat exchanger
1310 springs
1410 warm heat exchanger
1420 cold heat exchanger
1430 springs
1510 insulation
1520 warm heat exchanger
1530 cold heat exchanger
1540 springs
1610 insulation
1710 cooling unit
1720 insulation
1730 insulation
1740 insulation
1810 reagent compartment
1820 lanes
1830 device
1840 front opening
1910 fans for cold air circulation
1920 cold air outlet
1930 warm air inlet
1940 warm air 1950 cold air
2010 Fans for warm air circulation
2020 ambient air
2110 ambient air
2120 warm air
2130 cold air

What is claimed is:

1. A cooling device for attachment to a reagent compartment within an automated analyser system, comprising:
    a housing with a first side for attachment to the reagent compartment, and a second side away from the reagent compartment opposite to the first side; and
    a cooling unit that is assembled close to the second side of the housing so that the cooling unit is maximally separated from the reagent compartment, wherein the cooling unit comprises with at least one cooling element with a warm upper side and a cold lower side, that is equipped with a cold side heat exchanger, wherein the cooling element is arranged close to the second side so that the cooling unit is maximally separated from the reagent compartment, said cooling unit; and
    at least one first fan, at least one cold air channel and at least one cold air opening at the first side of the housing for circulating cold air between the at least one cooling element and the reagent compartment in a closed system, wherein the at least one first fan is arranged within the at least one cold air channel between the at least one cold air outlet and the cold lower side of the cooling element, and
    further comprising at the first side of the housing at least one warm air inlet channel arranged below and separated from the at least one cold air channel for taking up warm air from the compartment and guiding it to the cold lower side of the at least one cooling element.

2. The device according to claim 1, further comprising a warm heat exchanger comprising at least one second fan and at least one warm air channel arranged between the warm upper side of the at least one cooling element and at least one warm air opening at a second side of the housing.

3. The device according to claim 1, further comprising at least one ambient air channel arranged between at least one opening within a third side of the housing and the warm upper side of the cooling element for cooling down the warm upper side of the at least one cooling element.

4. The device according to claim 1, wherein warm upper side and cold lower side of the at least one cooling element are separated by an insulation from each other.

5. The device according to claim 1, wherein the at least one cooling element is a Peltier element.

6. The device according to claim 1, wherein a spacer separates warm upper side and cool lower side of the at least one cooling element.

7. The device according to claim 6, wherein a temperature sensor is integrated into the spacer.

8. The device according to claim 1, wherein a spring connects the warm upper side and the cold lower side of the at least one cooling element.

9. The device according to claim 1, wherein the at least one cooling element is shaped in manner ensuring the correct orientation with a warm upper side and a cold lower side of the at least one cooling element.

10. A system for cooling a reagent compartment comprising:
    a reagent compartment, and
    a device for cooling a reagent compartment comprising:
        a housing with a first side for attachment to the reagent compartment, and a second side away from the reagent compartment opposite to the first side;
        a cooling unit with at least one cooling element with a warm upper side and a cold lower side, that is equipped with a cold side heat exchanger, wherein the cooling element is arranged close to the second side so that the cooling unit is maximally separated from the reagent compartment, said cooling unit;
        at least one first fan, at least one cold air channel and at least one cold air opening; at the first side of the housing for circulating cold air between the at least one cooling element and the reagent compartment in a closed system, wherein the at least one first fan is arranged within the at least one cold air channel between the at least one cold air outlet and the cold lower side of the cooling element, and
        further comprising at the first side of the housing at least one warm air inlet channel arranged below and separated from the at least one cold air channel for taking up warm air from the compartment and guiding it to the cold lower side of the at least one cooling element.

11. A method for cooling a reagent compartment, wherein the method comprises the steps of:
    a. providing a device for cooling a reagent compartment comprising:
        i. a housing with a first side for attachment to the reagent compartment, and a second side away from the reagent compartment opposite to the first side, a cooling unit with at least one cooling element with a warm upper side and a cold lower side, that is equipped with a cold side heat exchanger, wherein the cooling element is arranged close to the second side so that the cooling unit is maximally separated from the reagent compartment, said cooling unit, at least one first fan, a at least one cold air channel and at least one cold air opening at the first side of the housing for circulating cold air between the at least one cooling element and the reagent compartment in a closed system, wherein the at least one first fan is arranged within the at least one cold air channel between the at least one cold air outlet and the cold lower side of the cooling element; and
        ii. at the first side of the housing at least one warm air inlet channel arranged below and separated from the at least one cold air channel for taking up warm air from the compartment and guiding it to the cold lower side of the at least one cooling element;
    b. running the at least one fan for warm air circulation and the at least one fan for cold air circulation, so that cold air circulates from the cold lower side of the at least one cooling element into the reagent compartment and the warm air coming from the compartment is circulated to the cold lower side of the at least one cooling element.

12. A method of using a cooling device comprising a housing with a first side for attachment to the reagent compartment, and a second side away from the reagent compartment opposite to the first side, a cooling unit with at least one cooling element with a warm upper side and a cold lower side, that is equipped with a cold side heat exchanger, wherein the cooling element is arranged close to the second side so that the cooling unit is maximally separated from the reagent compartment, at least one first fan, a at least one cold air channel and at least one cold air opening at the first side of the housing for circulating cold air between the at least one cooling element, wherein the at least one first fan is arranged within the at least one cold air channel between the at least one cold air outlet and the cold lower side of the cooling element and the reagent compartment in a closed system and at the first side of the housing at least one warm air inlet channel arranged below and separated from the at least one cold air channel for taking up warm air from the compartment and guiding it to the cold lower side of the at least one cooling element comprising the step of:

mounting the cooling device to a reagent compartment for cooling the reagent compartment.

* * * * *